(12) United States Patent
Sheridan et al.

(10) Patent No.: US 12,370,090 B2
(45) Date of Patent: Jul. 29, 2025

(54) NARROW-ORIFICE FOREIGN BODY EXTRACTION DEVICE

(71) Applicant: Oregon Health & Science University, Portland, OR (US)

(72) Inventors: David Sheridan, Portland, OR (US); Richard Weitzel, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 517 days.

(21) Appl. No.: 17/664,309

(22) Filed: May 20, 2022

(65) Prior Publication Data

US 2022/0370252 A1 Nov. 24, 2022

Related U.S. Application Data

(60) Provisional application No. 63/210,907, filed on Jun. 15, 2021, provisional application No. 63/191,898, filed on May 21, 2021.

(51) Int. Cl.
*A61B 1/227* (2006.01)
*A61F 11/20* (2022.01)
*A61M 1/00* (2006.01)
*A61B 1/00* (2006.01)

(52) U.S. Cl.
CPC .............. *A61F 11/20* (2022.01); *A61M 1/87* (2021.05); *A61B 1/00094* (2013.01); *A61B 1/227* (2013.01)

(58) Field of Classification Search
CPC ........ A61F 11/20; A61B 1/227; A61B 1/2275
USPC .................................................. 600/200–245
See application file for complete search history.

(56) References Cited

U.S. PATENT DOCUMENTS

| | | |
|---|---|---|
| 6,390,975 B1 * | 5/2002 | Walls ........................ A61B 1/32 |
| | | 600/200 |
| 2021/0220179 A1 * | 7/2021 | Rebella .............. A61B 1/00087 |

* cited by examiner

*Primary Examiner* — Eduardo C Robert
*Assistant Examiner* — Tara Rose E Carter
(74) *Attorney, Agent, or Firm* — Foster Garvey P.C.

(57) ABSTRACT

A narrow-orifice foreign body extraction device configured as a unitary article comprises a volumetric enclosure bounded by a frustoconical cone, which has inner and outer surfaces and an intermediate section positioned between an apertured cap section and an apertured base section. The inner surface defines a boundary of an interior chamber of the volumetric enclosure, and the inner and outer surfaces define between them a cone wall. An adhesive material is secured to at least part of the inner or outer surfaces at the cap section and comprises an apertured portion and a tail portion. The apertured portion has one or more adhesive apertures and adhesive-covered opposing inner and outer side surfaces, and the tail portion has an adhesive-covered inner tail surface extending along and bonding to at least part of the outer surface at the cap section to secure the adhesive material to the cap section.

23 Claims, 14 Drawing Sheets

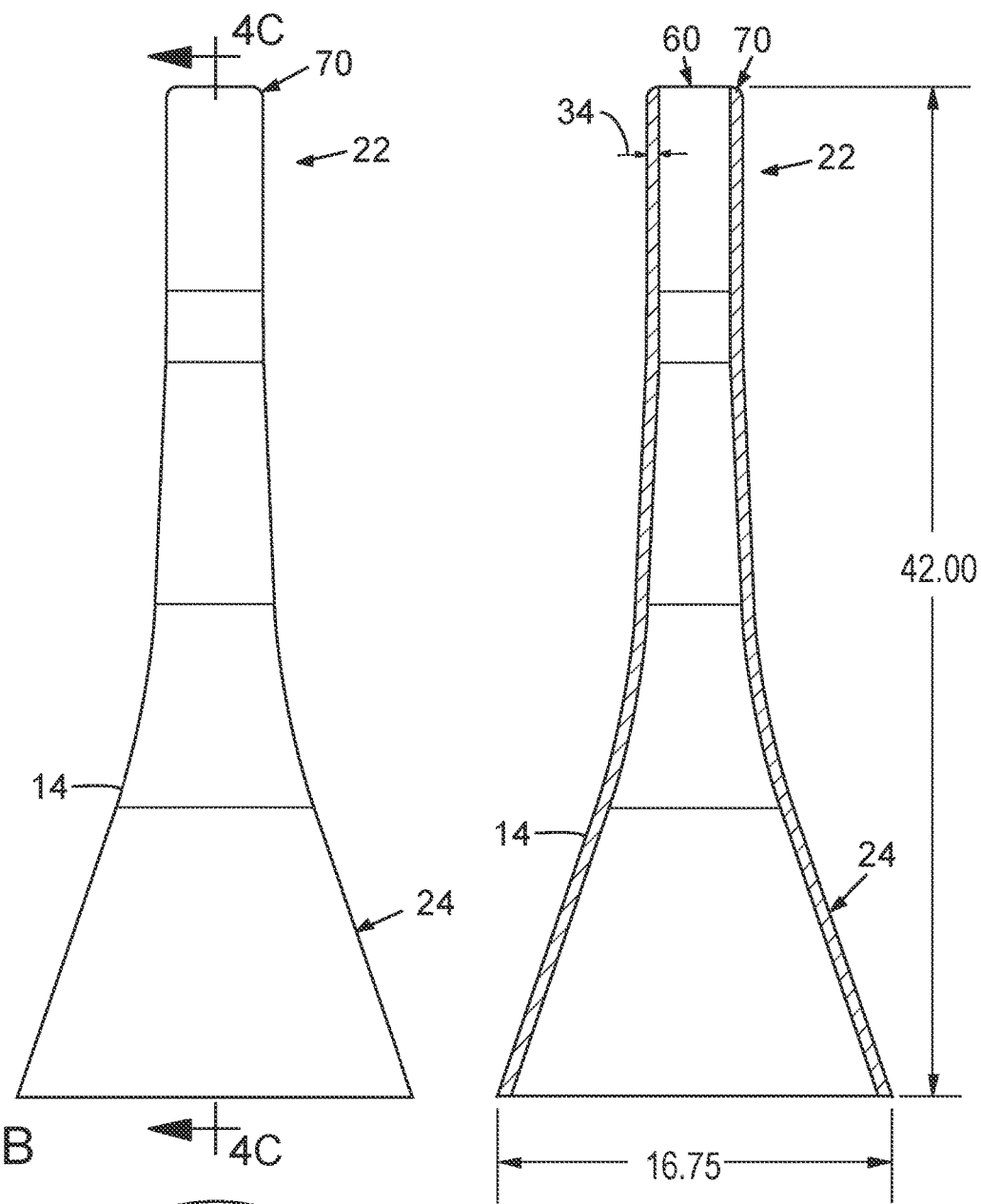
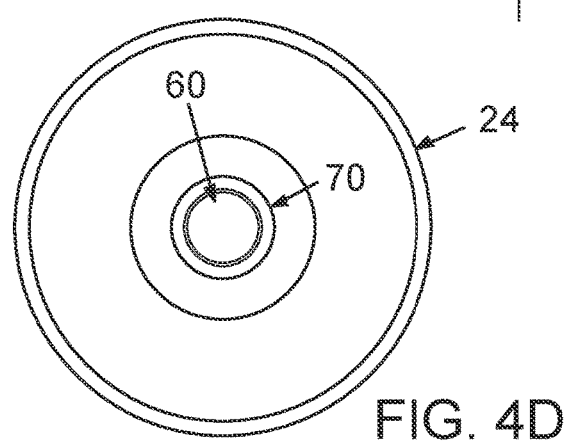
FIG. 4B
FIG. 4C
FIG. 4D

NARROW-ORIFICE FOREIGN BODY EXTRACTION DEVICE

COPYRIGHT NOTICE

© 2022 Oregon Health & Science University. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

BACKGROUND

Removal of foreign bodies from sensitive orifices such as ear canals or nasal passages is a difficult problem for both clinician and patient, especially children below the age of 14. A study between 2010-2016 showed that 85% of emergency department (ED) visits pertaining to ear foreign body removal were children ages 0-14, and of the 85%, 59% of the children were between the ages of 1-4 (Morris et al. (2018)). Although foreign body objects can get lodged in an individual of any age, children are less likely to fully comprehend the situation when they arrive in the ED. The inability to comprehend the strange setting and the potential discomfort caused by the foreign body could make the patient uncooperative during the extraction procedure.

Ideally, the object is removed after the first attempt, as additional attempts noticeably decrease chances of successful retrieval (Heim et al. (2007)). Current methods for extracting the foreign body utilize medical tools or irrigation during the extraction procedure that often do not result in extraction on the first attempt, potentially risking additional damage to the wall of the ear canal or tympanic membrane (i.e., ear drum) and risking breaking the object down into multiple parts, further complicating the procedure. If the physician is unable to remove the object, the patient is generally referred to an otorhinolaryngologist (ENT) or scheduled for an emergency operation, both costly alternatives.

Ear canals and nasal passages are small and sensitive areas, making it difficult to remove objects without causing further injury. The tight space restricts use of both an otoscope (for visualization, magnification, and illumination) and the removal tool (e.g., forceps, hooks, irrigation tubes). Therefore, physicians must remove the object without visualization and magnification. Without proper visualization, the tools used for removal may, for example, scrape the walls of the ear canal or puncture the tympanic membrane, consequently causing ancillary damage. The risk of additional damage also increases when the patient is a child because there is no guarantee that the child will cooperate during the procedure and may not keep still once the tool enters the ear canal. The child's movements could cause the instrument to miss the foreign object and scratch the canal wall, causing more damage.

Moreover, due to the variety of foreign bodies commonly found, such as food, insects, toys, buttons, pieces of crayon, and small batteries (Heim et al. (2007), there is no universal retrieval method, leaving clinicians to rely on disparate extraction methods. Current retrieval methods such as mechanical extraction, adhesion, irrigation, and suction pose a risk of additional damage to the individual and do not work for every object. Mechanical extraction involves using forceps, curettes, or other related slender tools to grasp the foreign body by gently advancing the tool through the external auditory canal. Irrigation entails using a catheter and a syringe to slowly inject fluid into the canal until the foreign body is washed out. Suction involves a suction catheter and wall suction to make contact with the foreign body. The use of negative pressure will pull on the object to extract it. A specialized extraction method requires physicians to apply medical adhesive (i.e., glue) to the wood end of a cotton tip applicator and carefully maneuver the adhesive end through the ear canal to connect to the foreign body. The cotton tip applicator would remain in the ear canal until the glue dries and adheres to the object. Once the connection is solidified, the two are slowly pulled out together. This is important because not only is training on medical devices costly for the hospital, which in turn increases medical costs for customers, but also the environment of an emergency department can be very hectic. Healthcare providers constantly move in and out of rooms, with little time to spare in treating each individual patient.

Further, foreign bodies found in the ear canal are generally of different shapes, materials, and sizes. Suction is a popular removal method but is limited to specific materials and object shape. If suction were used to remove the object, a spherical or flat object would allow for a proper seal to form and make for a quick and simple removal process. However, the objects commonly found in the auditory canal could be of any texture and material, making removal difficult and unique to the individual. For example, rehydratable objects such as food may expand when subjected to fluids and, hence, cannot be removed using irrigation. Physicians also have to be careful when removing food objects because they can easily break into pieces when handled.

Ultimately, it would be in the physician's and patient's best interest if these objects were removed whole on the first extraction attempt. Ideally, a suitable device for extraction of a foreign body from either the nose or the auditory canal would facilitate a high rate of such first-attempt extraction on a broad range of foreign bodies having different shapes and textures, consequently decreasing need for costly referral to outside specialist or the operating room and improving the patient's ultimate outcome. Moreover, a suitable device would be easy to operate and would not increase procedure time for physicians working under an already tight schedule. Integration of a suitable device with already existing medical equipment could utilize clinicians' pre-existing skills to minimize procedural time.

Aspects and advantages of the disclosed foreign body extraction device will be apparent from the following detailed description of preferred embodiments, which proceeds with reference to the accompanying drawings.

BRIEF DESCRIPTION OF THE DRAWINGS

FIG. 4B is a side elevation view of the extraction device of FIG. 4A shown without feature dimensions; FIG. 4C is a sectional view taken along lines 4C-4C of FIG. 4B; and FIG. 4D is a top plan view of the extraction device of FIGS. 1A and 1B.

DETAILED DESCRIPTION OF PREFERRED EMBODIMENTS

Figure 1A:
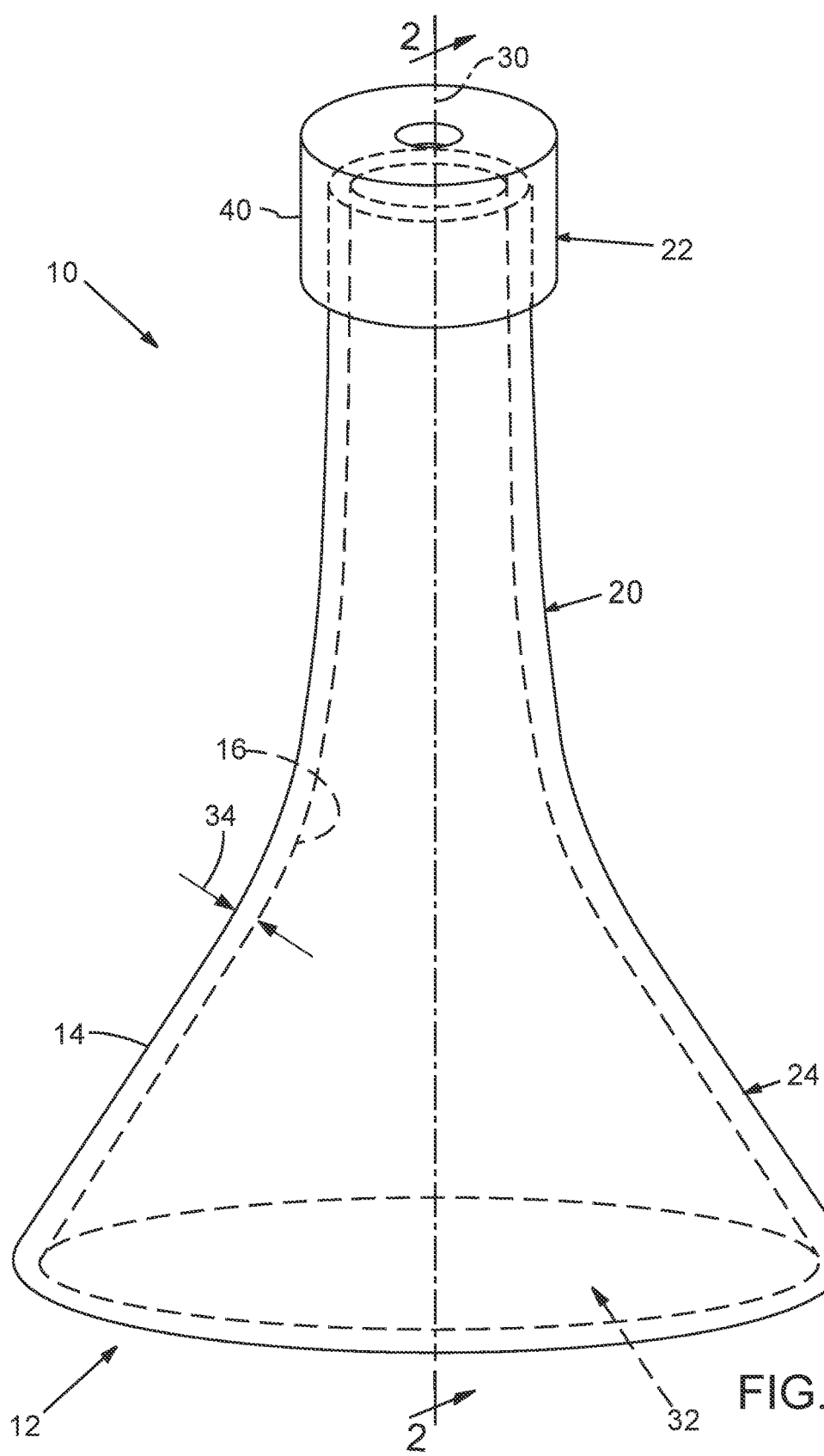
FIG. 1A is an oblique isometric view with phantom lines showing a narrow-orifice foreign body extraction device having an apertured cap section.
Figure 1B:
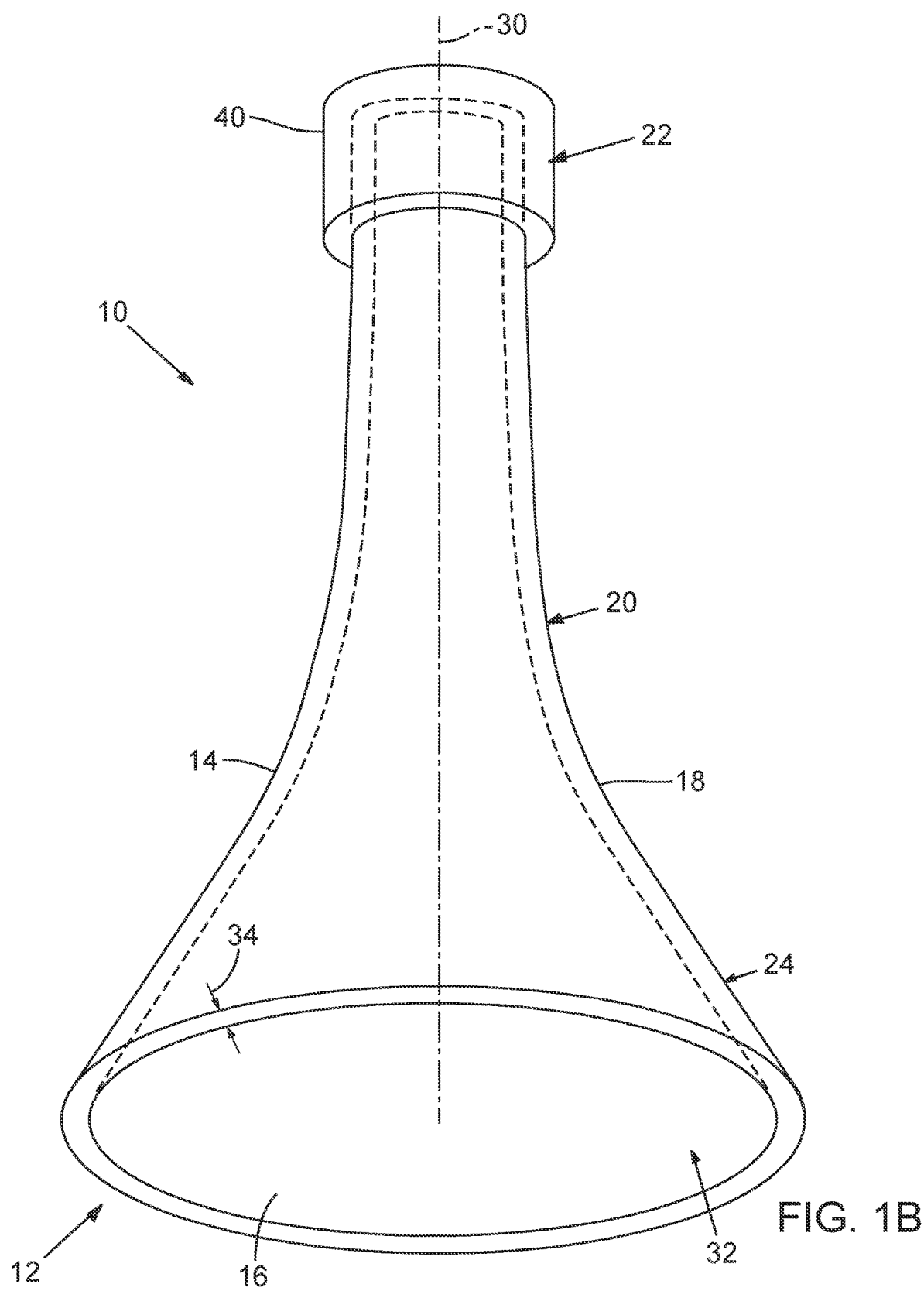
FIG. 1B is an oblique isometric view showing an opposing apertured base section.

FIGS. 1A and 1B are, respectively, oblique isometric views with phantom lines showing a narrow-orifice foreign body extraction device 10 at, respectively, opposing apertured cap and base sections. As shown in FIGS. 1A and 1B, extraction device 10 includes a volumetric enclosure 12 bounded by a frustoconical cone 14. Frustoconical cone 14 has an inner surface 16, an outer surface 18, and an intermediate section 20 positioned between an apertured cap section 22 and an apertured base section 24. Volumetric enclosure 12 defines a central longitudinal axis 30 that extends through base section 24, intermediate section 20, and cap section 22. Inner surface 16 defines the boundary of an interior chamber 32; and inner surface 16 and outer surface 18 define between them a cone wall 34. An adhesive material 40 is secured to at least part of inner surface 16 or outer surface 18 at cap section 22.

Figure 2:
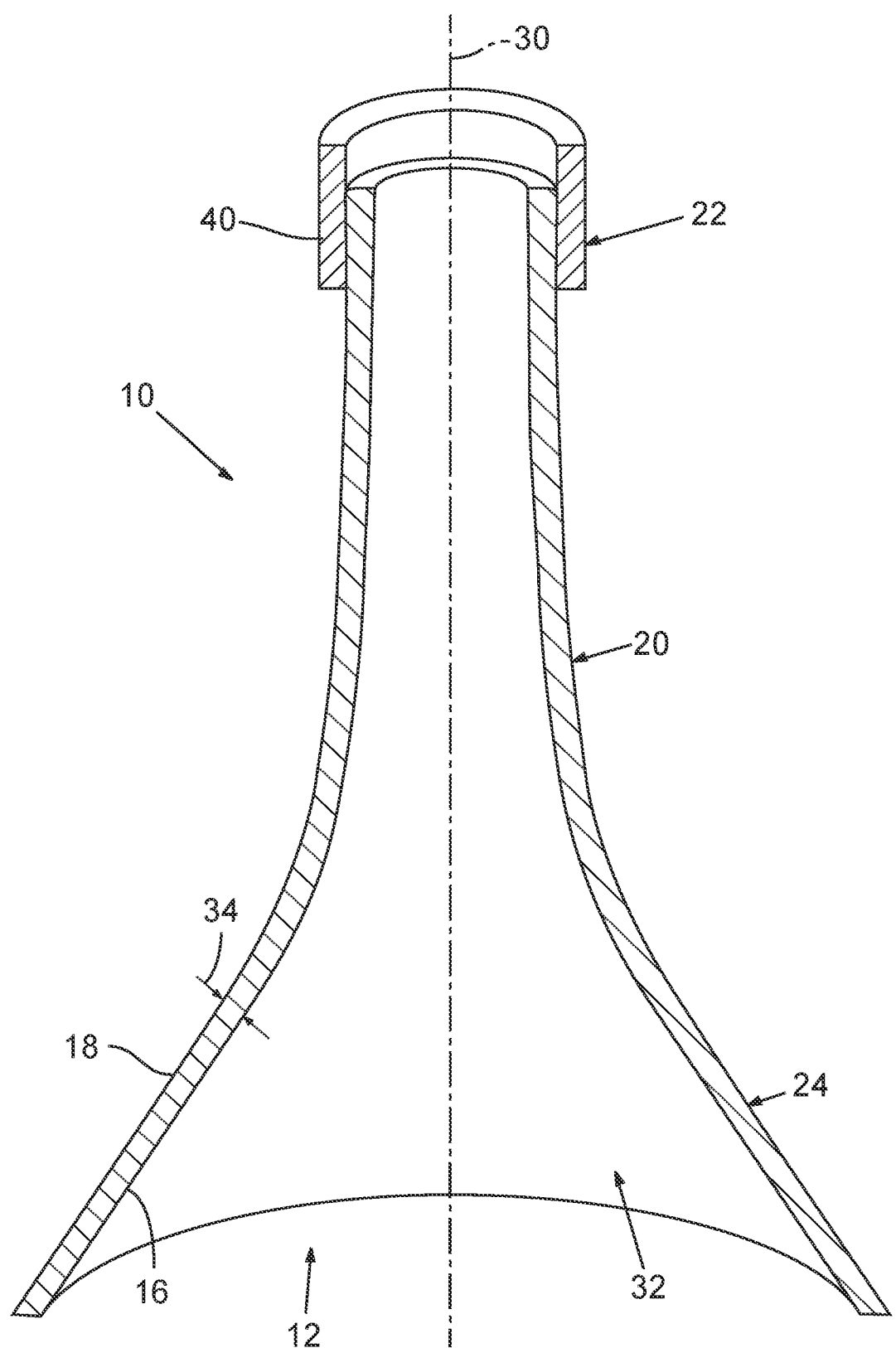
FIG. 2 is sectional view taken along lines 2-2 of FIG. 1A.

FIG. 2 is sectional view taken along lines 2-2 of FIG. 1A showing inner surface 16 defining the boundary of interior chamber 32 of volumetric enclosure 12. As shown in FIG. 2, inner surface 16 and an outer surface 18 define between them cone wall 34, and adhesive material 40 is secured to at least part of outer surface 18 at cap section 22. In some embodiments, adhesive material 40 may be secured to at least part of inner surface 16 at cap section 22 (FIGS. 7A, 7B, 7C, and 7D).

In some embodiments, at least one section selected from cap section 22, intermediate section 20, and base section 24 of frustoconical cone 14 is substantially shaped as a frustoconical hyperboloid, pseudosphere, or parabolic cone. In some embodiments, interior chamber 32 has a radius originating from central longitudinal axis 30 configured to increase continuously, incrementally, or both continuously and incrementally, along the length of cone wall 34 from cap section 22 to base section 24 to form a tapered cone.

Figure 10A:
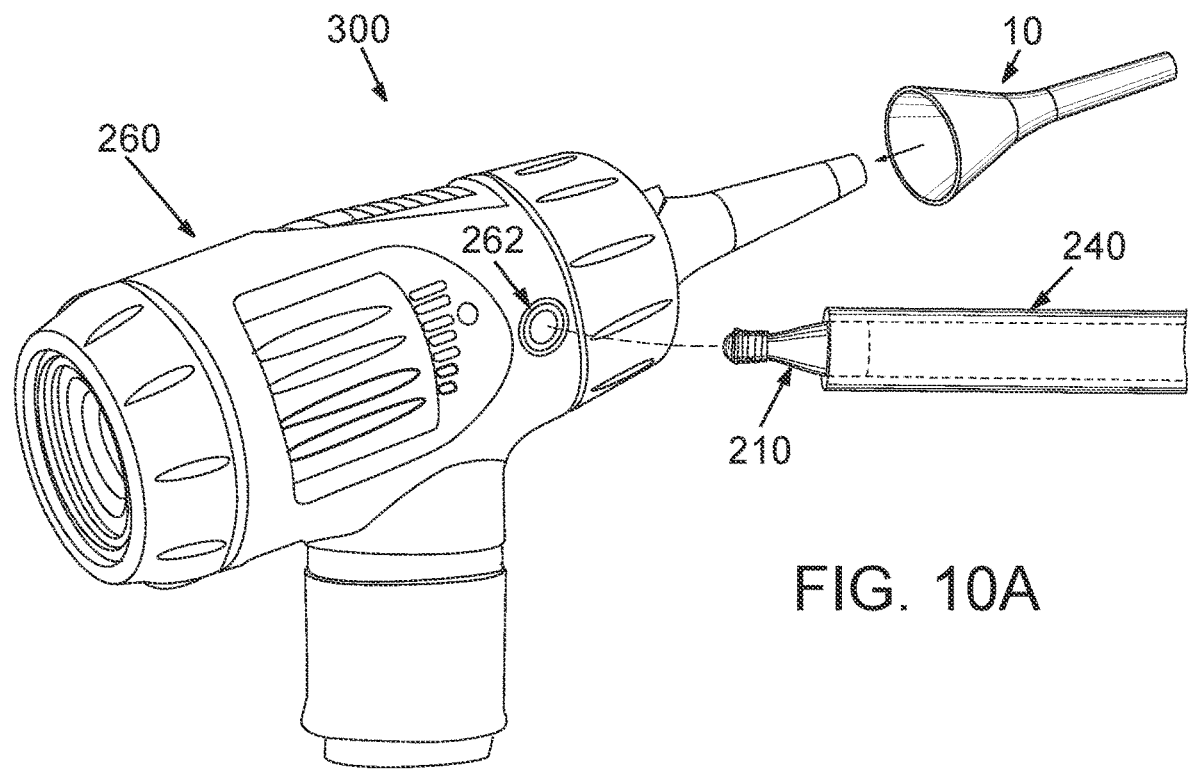
FIG. 10A is an exploded oblique view of a visualization device, the disclosed extraction device, and a vacuum adapter arranged for assembly as a system for extracting a foreign body from a narrow orifice.
Figure 10B:
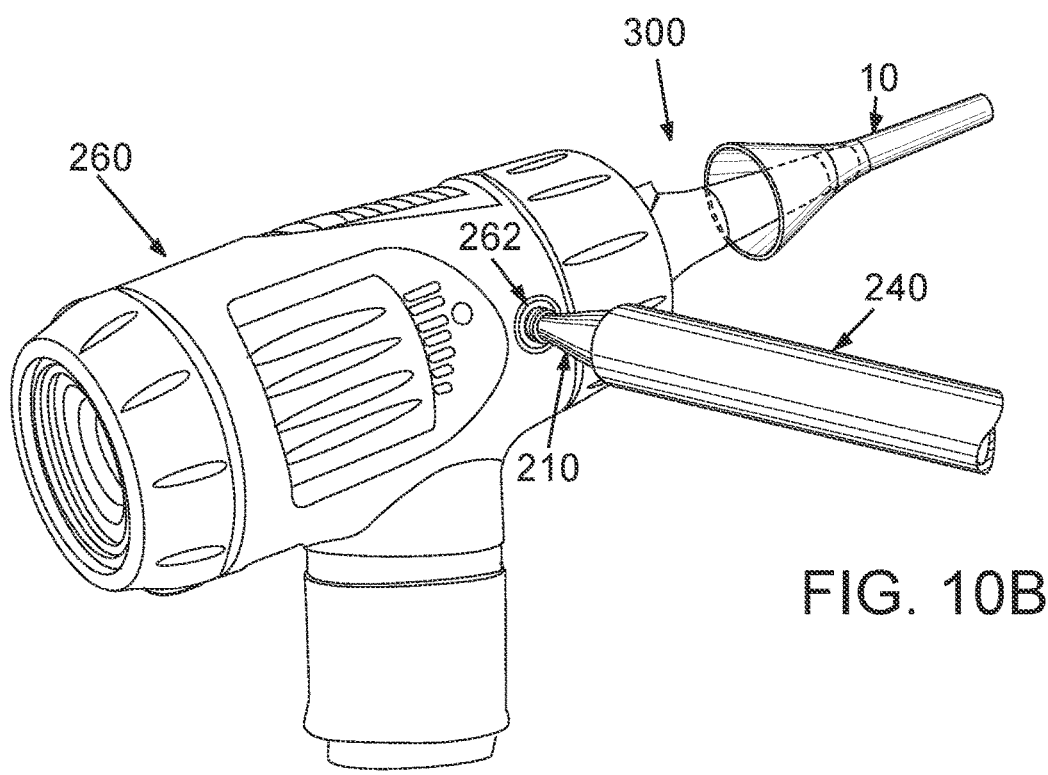
FIG. 10B is an oblique view of the system of FIG. 10A after assembly.

In some embodiments, cap section 22 comprises a set of one or more cap apertures (only one cap aperture shown) that extend through cone wall 34 into interior chamber 32 at cap section 22. In some embodiments, each aperture in the set of cap apertures has a diameter of about 0.01 mm to 1.00 mm, about 1.00 mm to 2.00 mm, about 2.00 mm to 3.00 mm, about 3.00 mm to 4.00 mm, or about 4.00 mm or greater. In some embodiments, interior chamber 32 of frustoconical cone 14 at cap section 22 has a diameter of about 1.00 mm to 2.00 mm, about 2.00 mm to 3.00 mm, about 3.00 mm to 4.00 mm, or about 4.00 mm or greater. In some embodiments, interior chamber 32 of frustoconical cone 14 at intermediate section 20 has a diameter of about 1.00 mm to about 8.00 mm. In some embodiments, interior chamber 32 of frustoconical cone 14 at base section 24 has a diameter of about 1.00 mm to about 30.00 mm. In some embodiments, base section 24 is configured to form a friction fit with a head of an otoscope (FIGS. 10A and 10B). In some embodiments, base section 24 comprises a set of one or more base apertures (only one base aperture shown) that extend through cone wall 34.

Figure 3A:
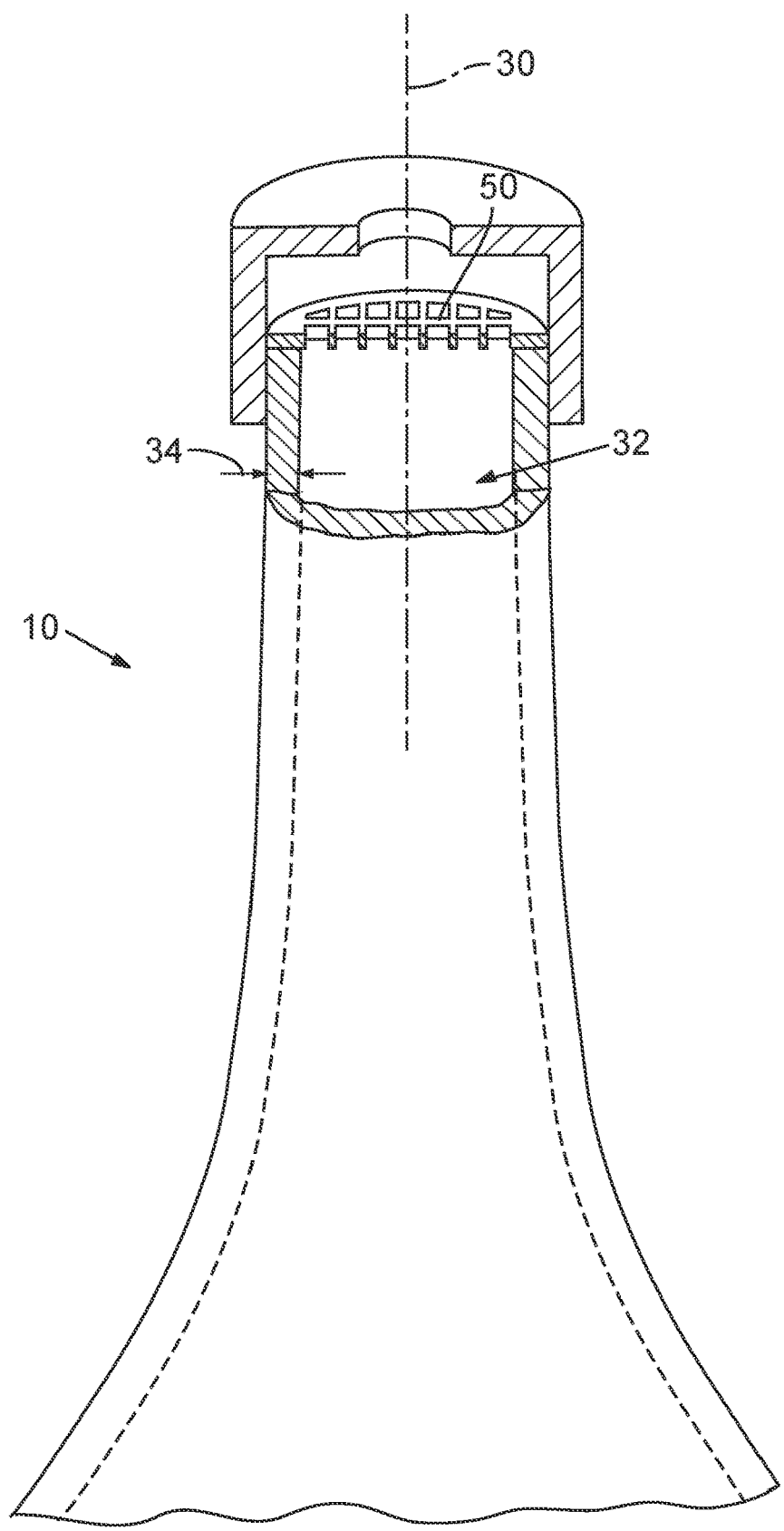
FIG. 3A is an oblique isometric view of an alternative embodiment of the disclosed extraction device with a portion of the apertured cap section and cone wall cut away to show a perforated platform set within an interior chamber of the extraction device in transverse relation to a central longitudinal axis.

FIG. 3A is an oblique isometric view of an alternative embodiment of the disclosed extraction device of FIGS. 1A and 1B, with a portion of cone wall 34 cut away to show a perforated platform 50 set within interior chamber 32 of extraction device 10 in transverse relation to central longitudinal axis 30.

Figure 3B:
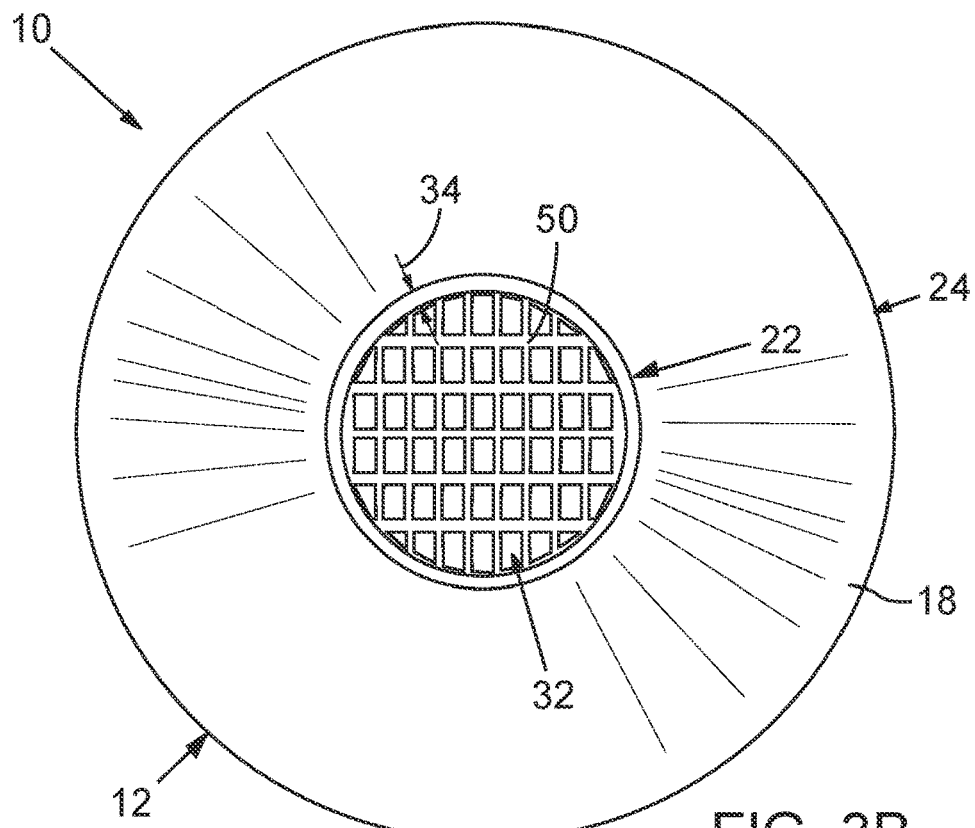
FIGS. 3B and 3C are, respectively, top and bottom plan views showing the perforated platform of the extraction device of FIG. 3A set within the interior chamber of the extraction device.
Figure 3C:
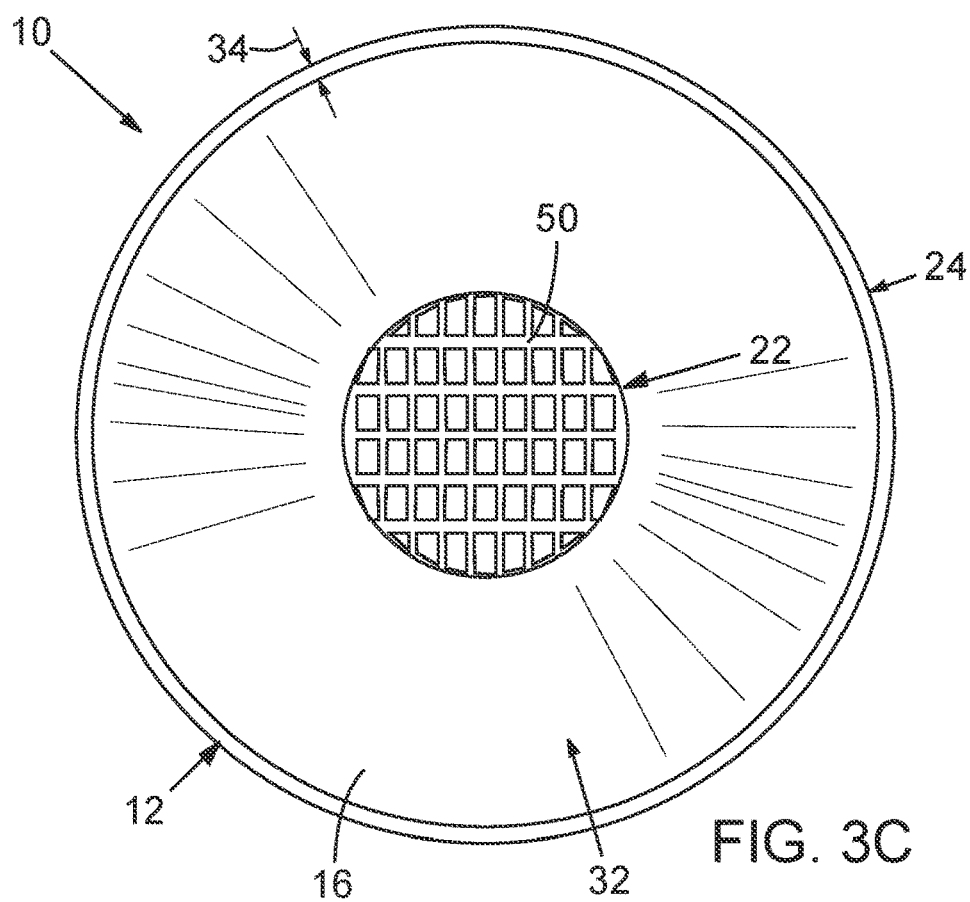

FIGS. 3B and 3C are, respectively, top and bottom plan views showing perforated platform 50 of the extraction device of FIG. 3A set within interior chamber 32. As shown in FIG. 3B, perforated platform 50 is set within interior chamber 32 at cap section 22 to facilitate the capture of foreign bodies brought within interior chamber 32 by relatively negative pressurized air flowing into interior chamber 32 from cap section 22 to base section 24. In some embodiments, relatively negative pressurized air is applied from base section 24 to draw ambient air into cap section 22 and through perforated platform 50 towards a source 240 (FIGS. 10A and 10B) of relatively negative pressurized fluid in the form of gas, preferably air, operatively connected to base section 24.

Skilled persons will understand that perforated platform 50 may be formed as an integral part of inner surface 16 of cone wall 34. In some embodiments, perforated platform 50 comprises an adhesive to secure foreign bodies drawn into interior chamber 32 by air flowing towards negative air-pressure source 240.

Figure 4A:
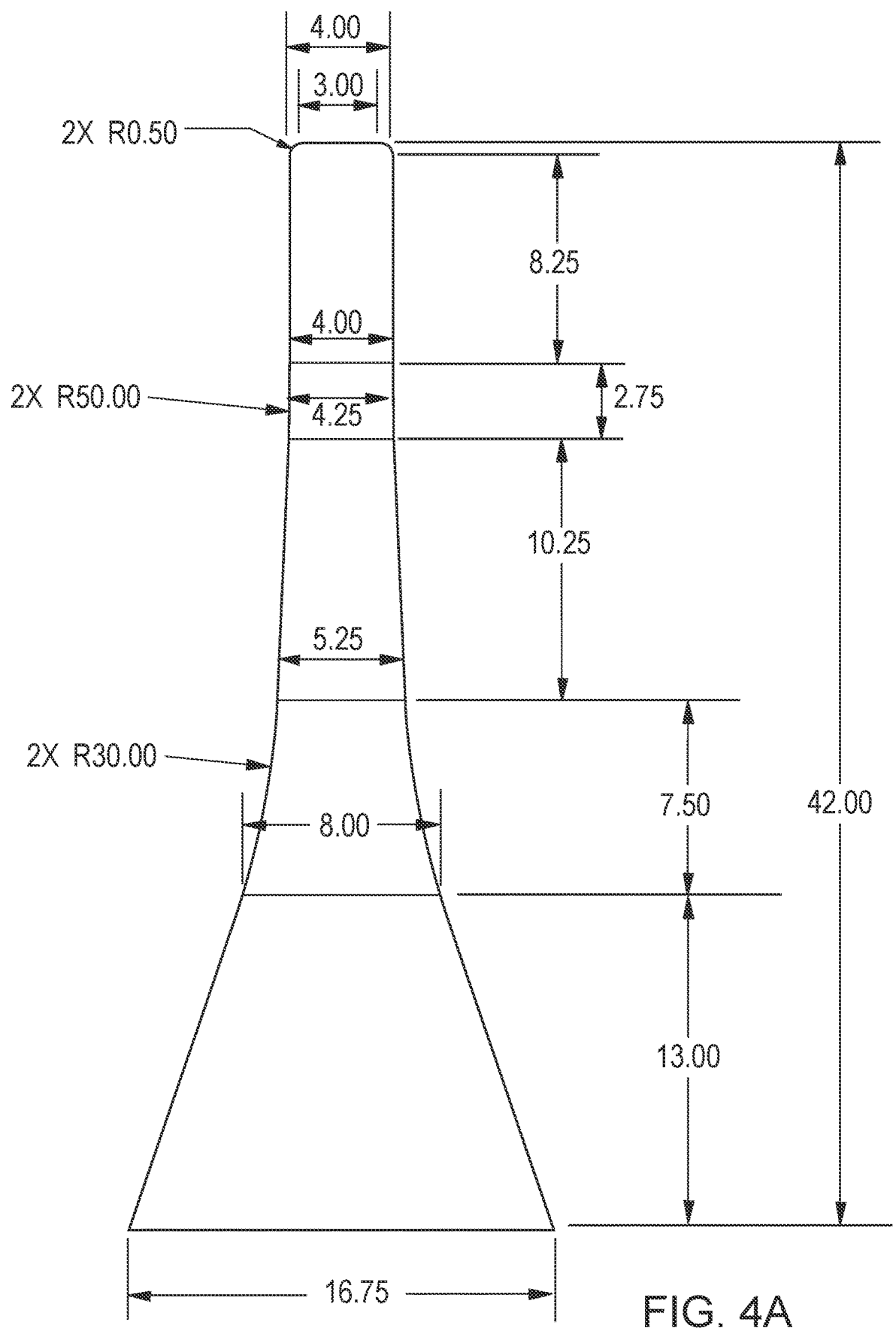
FIG. 4A shows size and feature dimensions superimposed on a side elevation view of the extraction device of FIGS. 1A and 1B.

FIG. 4A shows size and feature dimensions superimposed on a side elevation view of the extraction device of FIGS. 1A and 1B; FIG. 4B is a side elevation view of the extraction device of FIG. 4A shown without feature dimensions; FIG. 4C is a sectional view taken along lines 4C-4C of FIG. 4B; and FIG. 4D is a top plan view of the extraction device of FIGS. 1A and 1B. The numerical dimensions shown are expressed in millimeters. As shown in FIGS. 4B, 4C, and 4D, cone wall 34 at cap section 22 forms an annular rim 70 encompassing one or more of the cap apertures in a set of cap apertures 60. In some embodiments, annular rim 70 has a radius of curvature of about 2×R0.10 to about 2×R1.00.

In a preferred embodiment, the length of frustoconical cone 14 is about 42.00 mm and the width of frustoconical cone 14 is about 16.75 mm. In some embodiments, the length of frustoconical cone 14 is about 25.00 mm to about 50.00 mm. In some embodiments, the width of frustoconical cone 14 at base section is about 10.00 mm to about 20.00 mm.

In some embodiments, cone wall 34 at cap section 22 has a radius of curvature of about 2×R30.0 to about 2×R90.0. In some embodiments, cone wall 34 at intermediate section 20 or base section 24 has a radius of curvature of about 2×R10.0 to about 2×R70.0. In some embodiments, the diameter of interior chamber 32 is about 1.00 mm to about 30.00 mm. In some embodiments, cone wall 34 has a thickness of about 0.01 mm to 0.25 mm, about 0.25 mm to 0.75 mm, or about 0.75 mm or greater.

Figure 5:
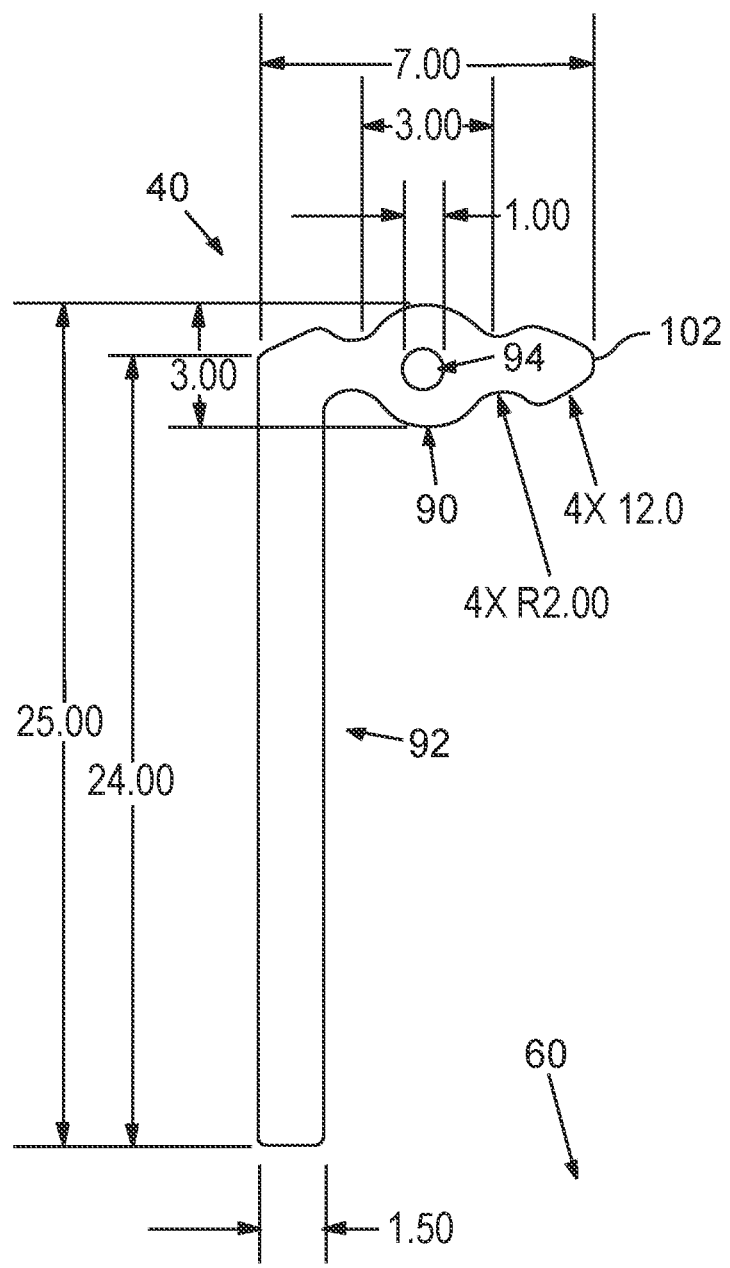
FIG. 5 shows size and feature dimensions superimposed on a plan view of an adhesive material having an apertured portion and a tail portion.

FIG. 5 shows size and feature dimensions superimposed on a plan view of a preferred embodiment of an adhesive material 40 having an apertured portion 90 and a tail portion 92. The numerical dimensions shown are expressed in millimeters. As shown in FIG. 5, in a preferred embodiment, apertured portion 90 has a set of one or more adhesive apertures 94 (only one aperture shown) having a diameter of about 1.00 mm. In some embodiments, set of adhesive apertures 94 comprises apertures having a diameter of about 2.00 mm. In some embodiments, apertured portion 90 of adhesive material 40 has a length of about 1.00 mm to about 10.0 mm (7 mm shown), a width of about 1.00 mm to about 10.0 mm (3 mm shown), and a thickness of about 0.01 mm to about 2.00 mm. In some embodiments, tail portion 92 of adhesive material 40 has a length of about 1.00 mm to about 50.0 mm (24.00 mm shown), a width of about 0.01 mm to about 3.00 mm (1.50 mm shown), and a thickness of about 0.01 mm to about 2.00 mm. In a preferred embodiment, at least one aperture in set of adhesive apertures 94 and at least one aperture in set of cap apertures 60 are substantially spatially aligned to provide an unobstructed sightline through cap section 22 and adhesive material 40.

Figure 6:
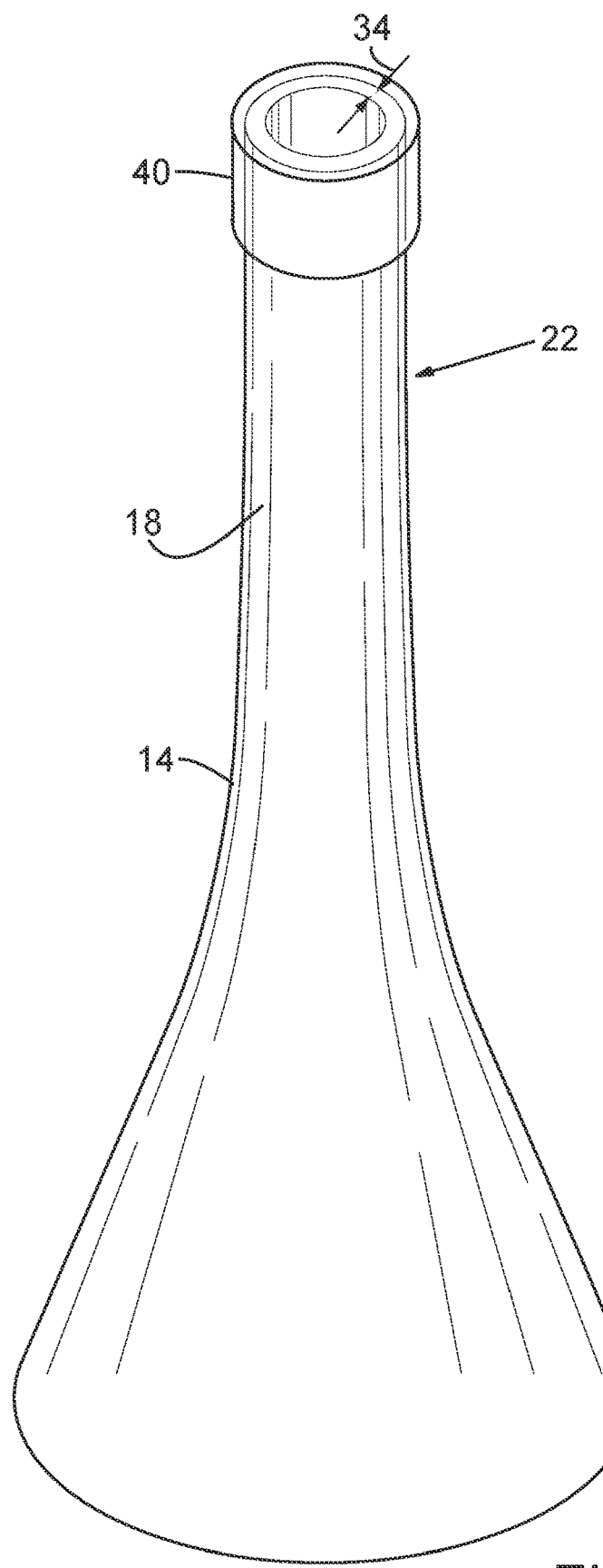
FIG. 6 is an oblique side view of an extraction device having its adhesive material secured to part of the outer surface of the cap section.

FIG. 6 is an oblique side view of extraction device 10 having adhesive material 40 secured to and wrapped around part of outer surface 18 of cap section 22. As shown in FIG. 6, cone wall 34 of frustoconical cone 14 may comprise a biocompatible plastic. Skilled persons will understand that cone wall 34 may comprise rubber, ceramic, wood, paper, composite, or other suitable material.

Figure 7A:
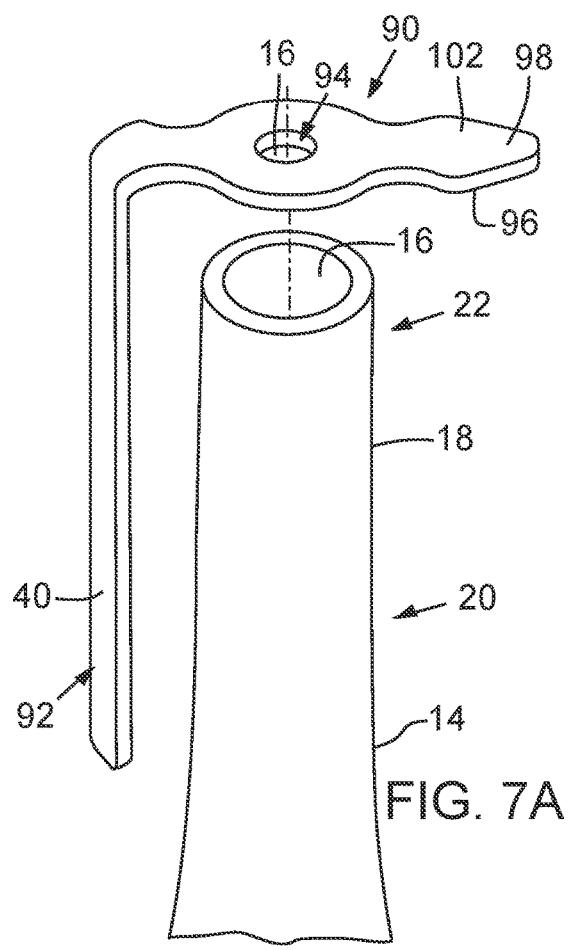
FIGS. 7A, 7B, 7C, and 7D are fragmentary oblique views showing in phantom lines of an adhesive material being applied step by step to a cap section of an extraction device.
Figure 7B:
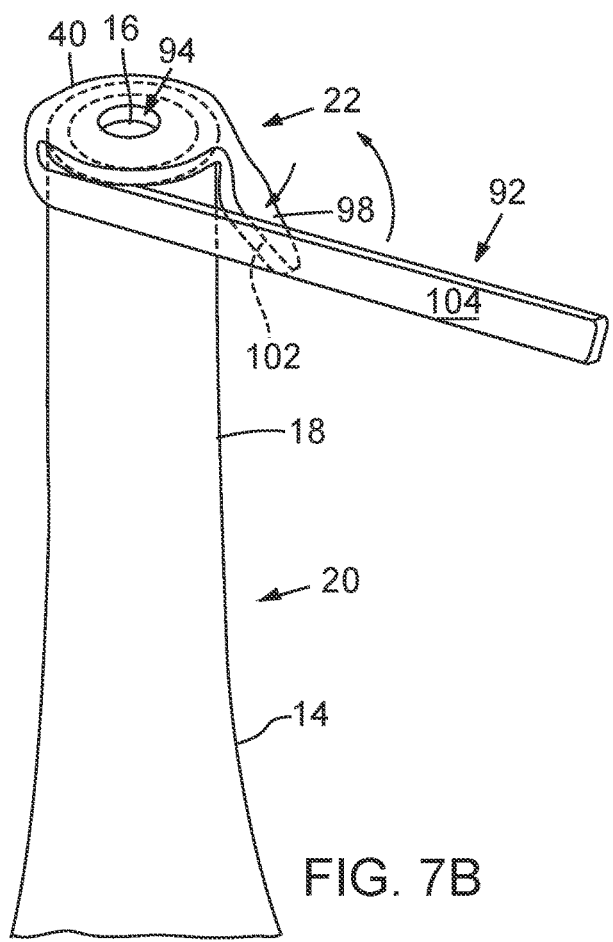

FIGS. 7A, 7B, 7C, and 7D are fragmentary oblique views showing in phantom lines adhesive material 40 being applied step by step to cap section 22 of frustoconical cone 14 of extraction device 10. As shown in FIG. 7A, apertured portion 90 has an adhesive-covered inner side surface 96 and an opposing adhesive-covered outer side surface 98. In some embodiments, tail portion 92 has an adhesive-covered inner tail surface 100 (FIG. 7C) that extends along, and bonds to, at least part of outer surface 18 at cap section 22 to secure adhesive material 40 to cap section 22.

Figure 7C:
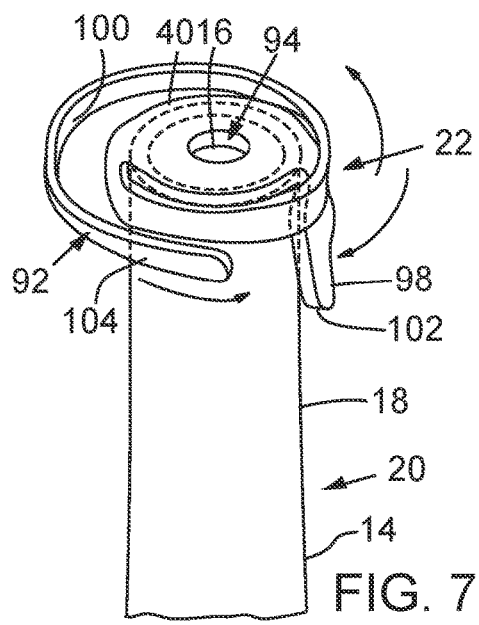
Figure 7D:
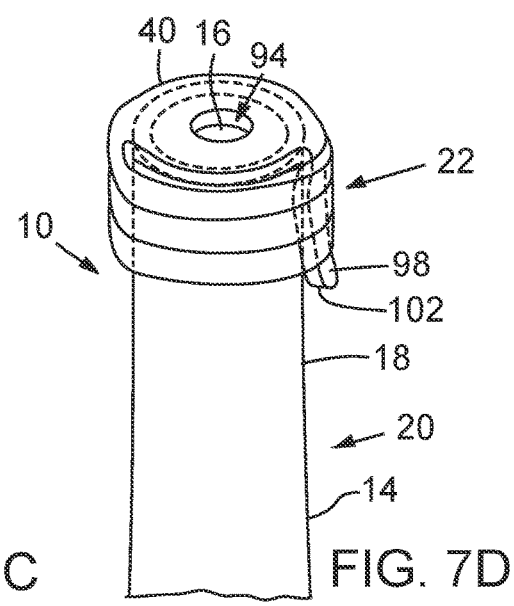

In some embodiments, adhesive material 40 is selectively applied by a user to inner surface 16 or outer surface 18 at cap section 22 of frustoconical cone 14. As shown in FIGS. 7C and 7D, adhesive-covered inner side surface 96 of apertured portion 90 is set on annular rim 70 of cap section 22. An end tab 102 of apertured portion 90 is folded and urged against outer surface 18 as tail portion 92 of adhesive material 40 is wrapped around cap section 22. Adhesive-covered inner tail surface 100 makes contact with outer side surface 98 of apertured portion 90 in successive contiguous rings around outer surface 18 in a direction downwardly along longitudinal axis 30 toward intermediate section 20 to secure adhesive material 40 to frustoconical cone 14 and thereby form extraction device 10. In a preferred embodiment, tail portion 92 has an essentially adhesive-less outer tail surface 104 to facilitate movement of extraction device 10 along the surface of a narrow orifice. In some embodiments, tail portion 92 may be secured to outer surface 18 of frustoconical cone 14 at intermediate section 20. In some embodiments, surface 104 of tail portion 92 is covered with a non-adhesive smooth-surface material, such as Parafilm® tape, to facilitate maneuvering extraction device 10 into a narrow orifice without adhering to the patient's tissue.

Figure 8A:
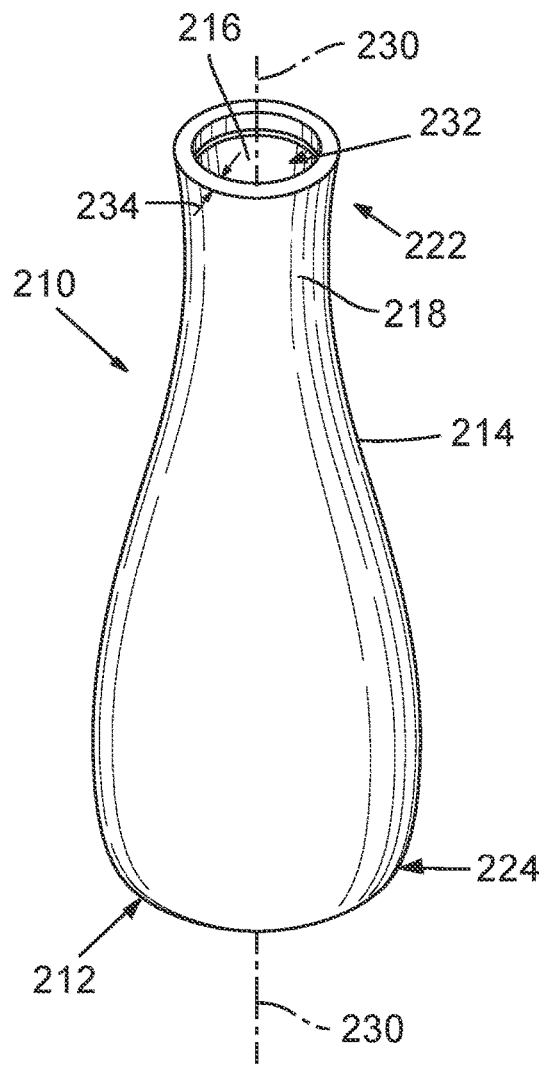
FIG. 8A is an oblique side view of a vacuum adapter for providing negative pressure to a visualization device.
Figure 8B:
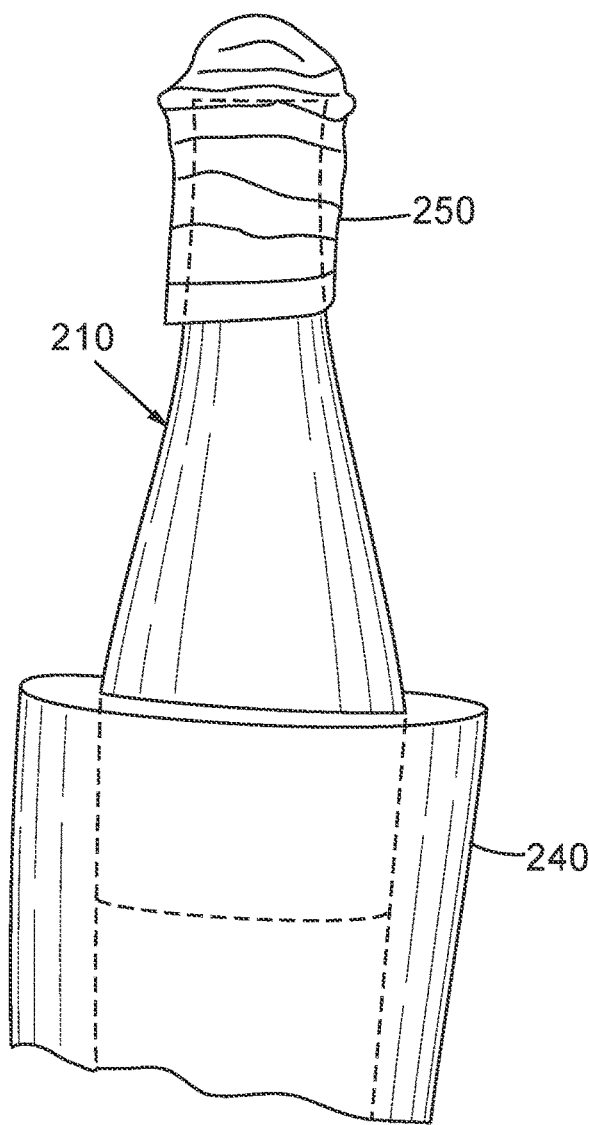
FIG. 8B is an oblique fragmentary view of the vacuum adapter of FIG. 8A attached to a negative pressure source of gas at a gas-pressure source adapter end to communicate relatively negative pressurized gas from the negative gas-pressure source.

FIG. 8A is an oblique side view of a vacuum adapter 210 for providing relatively negative pressurized air to a visualization device 260 (FIGS. 10A and 10B); and FIG. 8B is an oblique fragmentary view of the vacuum adapter of FIG. 8A attached to negative air pressure source 240. As shown in FIG. 8A, vacuum adapter 210 has a volumetric enclosure 212 bounded by a tubular adapter body 214. Adapter body 214 has an inner adapter surface 216 that defines the boundary of an interior chamber 232. Volumetric enclosure 212 has a visualization device adapter end 222 and a fluid-pressure source adapter end 224. Inner adapter surface 216 and an outer adapter surface 218 define between them an adapter wall 234. Volumetric enclosure 212 defines a central longitudinal axis 230 that extends through adapter ends 222 and 224. Adapter end 222 is configured to attach to visualization device 260, and adapter end 224 is configured to attach to negative air pressure source 240 to communicate relatively negative-pressurized air through extraction device 10, visualization device 260, and into negative air-pressure source 240. Skilled persons will understand that a visualization device may comprise an otoscope.

As shown in FIG. 8B, a Parafilm® tape wrap 250 is applied to adapter end 222 to create a seal between vacuum adaptor 210 and an insufflation port 262 (FIGS. 10A and 10B) of a visualization device 260. Skilled persons will understand that insufflation port 262 may communicate both relatively negative pressurized air as well as positive pressurized air.

Figure 9A:
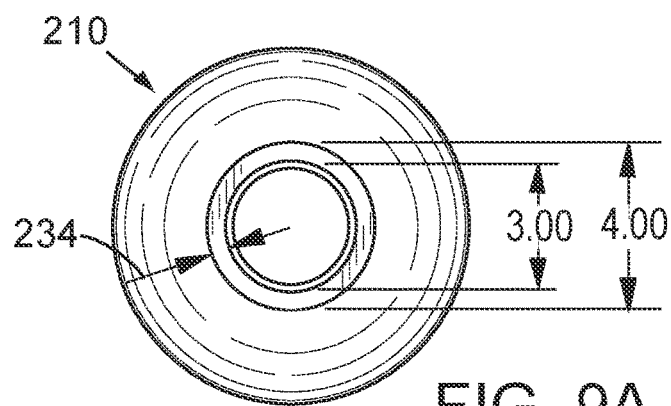
FIGS. 9A and 9B show, respectively, top plan and side elevation views of a vacuum adapter.
Figure 9B:
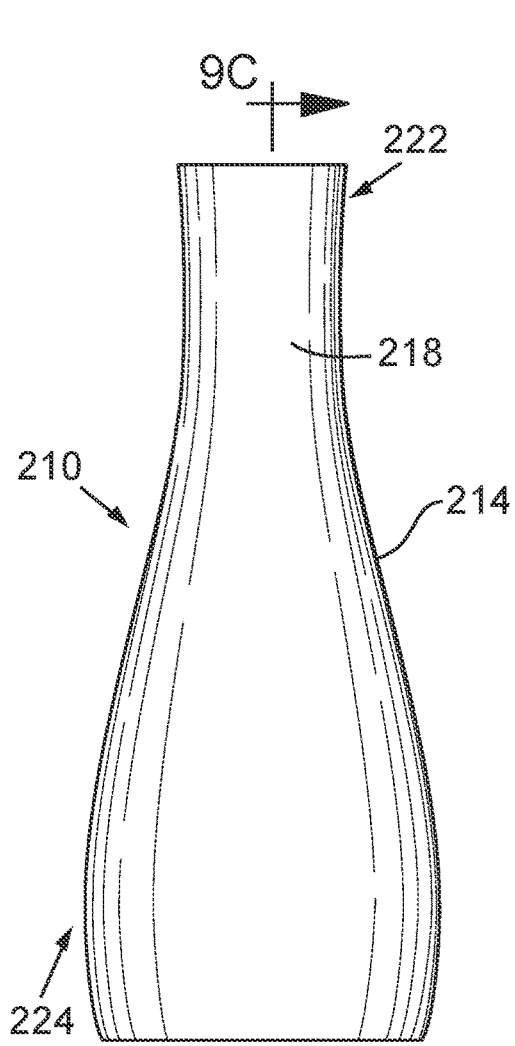
Figure 9C:
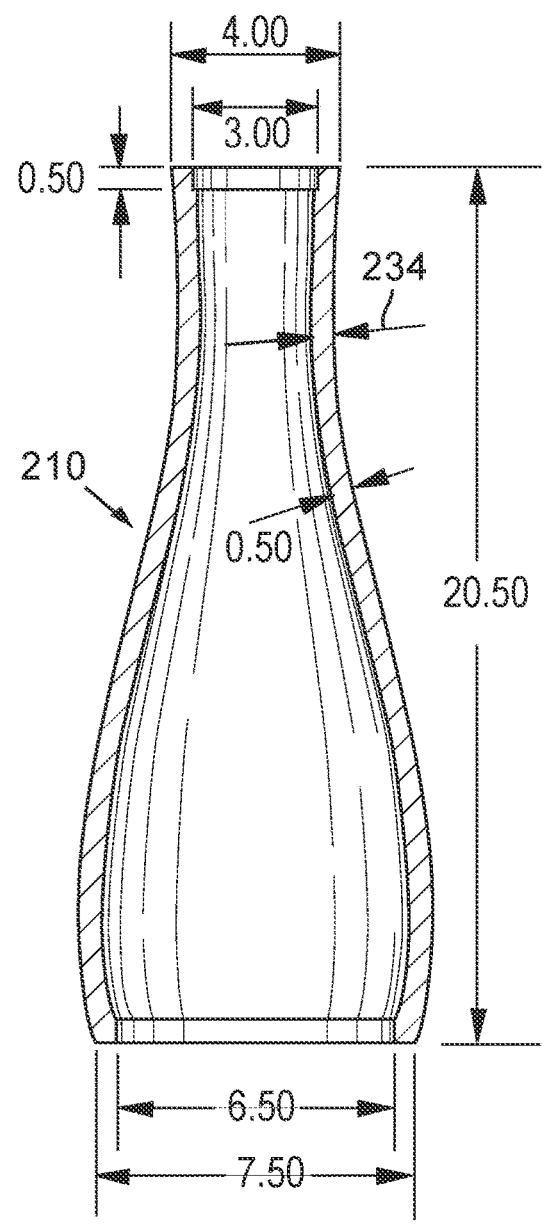
FIG. 9C is a sectional view taken along lines 9C-9C of FIG. 9B, with size and feature dimensions superimposed on FIGS. 9A and 9C.

FIGS. 9A and 9B show, respectively, top plan and side elevation views of vacuum adapter 210; and FIG. 9C is a sectional view taken along lines 9C-9C of FIG. 9B, with size and feature dimensions superimposed on FIGS. 9A and 9C. The numerical dimensions shown are expressed in millimeters. As shown in FIGS. 9A, 9B, and 9C, in a preferred embodiment, adapter wall 234 has width of about 0.50 mm. In some embodiments, adapter wall 234 may have a width of about 0.1 mm to about 3.00 mm.

FIG. 10A is an exploded oblique view of visualization device 260 having insufflation port 262, extraction device 10, and vacuum adapter 210 attached to negative pressure source 240 arranged for assembly as a system 300 for extracting a foreign body from a narrow orifice; and FIG. 10B is an oblique view of system 300 of FIG. 10A after assembly. In a preferred embodiment of extraction system 300, vacuum adapter 210 is configured to attach to insufflation port 262 of visualization device 260 and communicate relatively negative-pressurized air through extraction device 10 and visualization device 260 and into negative air-pressure source 240, thereby to facilitate removal of a foreign body from a narrow orifice.

In some embodiments, extraction device 10 and vacuum adapter 210 may be printed on a Formlabs 3D printer using a photoreactive resin. In some embodiments, a biodegradable material may be used to construct extraction device 10 and vacuum adapter 210. In some embodiments, extraction device 10 and vacuum adapter 210 may be formed using injection wells.

EXAMPLES

The following examples further describe and demonstrate use of preferred embodiments of the disclosed extraction device 10. The examples are given solely for the purpose of illustration and are not to be construed as limiting use of extraction device 10 because many variations are possible without departing from the spirit and scope of its uses.

For all experimental procedures disclosed herein, a clear vinyl tube (Ø 6 mm) and a sponge were used to model a pediatric ear canal, and an otoscope was used as a visualization device. During testing, it was noted that the force required to detach adhesive material 40 from the inner wall of the vinyl tube was large, making the removal of the foreign object difficult. In some instances, if adhesive material 40 stuck to the inner wall of the vinyl tube during removal, the force required to remove adhesive material 40 would cause the foreign object to disconnect from adhesive material 40. Skilled persons will understand that the vinyl tube and sponge could be replaced with Lorica™ soft leather to offer a more accurate representation of the skin in the ear canal and that the tympanic membrane could be represented by nitrile rubber gloves, Kimwipes® cleaning wipes, or laboratory stretch film (e.g., Parafilm®) tape.

For all experimental procedures disclosed herein, a Parafilm® wrap 250 was used to create a seal between the vacuum adapter 210 and the head of an otoscope during testing (as shown in FIG. 8B). Skilled persons will understand that Parafilm® tape could be replaced with sealing materials having a thickness similar to that of Parafilm® tape. In preferred embodiments, extraction device 10 fits into a 6 mm diameter ear canal. Although the thin Parafilm® wrap did not significantly increase the thickness of adapter end 224 of vacuum adapter 210, skilled persons will understand that alternative materials may achieve an essentially equivalent seal without adding excessive thickness to adapter end 224.

For all experimental procedures disclosed herein, extraction device 10 was printed on a Formlabs 3D printer using a photoreactive resin. The 3D printer accurately formed the photoreactive resin to the shape of extraction device 10, producing extraction device prototypes that were less prone to breakage than prototypes printed in Polylactic Acid (PLA) or Acrylonitrile Butadiene Styrene (ABS) material.

Example 1—Removing a Foreign Body from a Patient's Ear Canal

To facilitate extraction efficiency and minimize harm to a patient's ear canal during extraction, there are several factors to consider. For example, the ear canal in children is very narrow and approximately 2.5 centimeters long. The canal is dark and difficult to visualize clearly with the naked eye. Current technique for visualizing the ear canal entails use of an otoscope that contains a lens for magnification and a light for illumination. This allows for both a detailed and an illuminated view of the whole ear canal up to the tympanic membrane. Therefore, a preferred embodiment of extraction device 10 has a similar form of visualization to current techniques so a physician or other medical professional has a clear view of the working field while attempting to retrieve the foreign body. For example, the most common types of objects that get stuck in a child's ear are varied in material properties. A preferred embodiment of extraction device 10 is capable of fixating against several different shapes and textures of a foreign body to facilitate retrieving it effectively on the first attempt. In a preferred embodiment, extraction device 10 is sufficiently long enough to reach the end of an ear canal in the case of a foreign body that is lodged against the tympanic membrane.

Foreign bodies stuck at the end of an ear canal have proven to be the most difficult for emergency department physicians or other medical professionals to remove and tend to be out of their capability to resolve, requiring outside referral. Thus, a preferred extraction device 10 is configured to interact extremely close to the tympanic membrane without perforating it. Perforating the tympanic membrane can be incredibly painful and result in hearing loss. For example, in a preferred embodiment, negative pressure communicating through extraction device 10 should not exceed 200 mmHg to avoid damaging the tympanic membrane.

Verification testing of the extraction device 10 was performed to ensure that design inputs identified in a design traceability matrix (Table 1) were satisfied in a preferred prototype design. The design traceability matrix comprised a process of identifying top level user and sub-user needs related to removing foreign bodies from the auditory canal of a subject. The design inputs comprised testable or observable design features selected to meet the top-level user and sub-user needs recorded in Table 1. As referred to herein, "top level user needs" and "sub-user needs" refer to design features selected in response to the subjective feedback of the user. For example, the design traceability matrix identified five top level user needs related to removing foreign bodies: (1) the ability to visualize the working space, (2) the ability to retrieve most common foreign bodies found in ears, (3) a proposed extraction device be biocompatible, (4) a proposed extraction device be configured so as to not puncture or press hard against the tympanic membrane of a subject, and (5) the proposed extraction device be intuitive and/or user friendly. Top level users included medical practitioners such as physicians and engineers. Skilled persons will understand that removal of foreign bodies from auditory canals is a procedure that may be within the scope of practice of many medical professionals, including physicians, physician assistants, nurse practitioners, nurses, or any other medical professional having a similar scope of practice.

As referred to herein, "design inputs" refer to testable or observable features of a proposed extraction device that could be measured or verified. For example, the design inputs selected in in response to top level user need (1) (the ability to visualize the working space) included: (a) if the light source of a proposed extraction device met or exceeded a 3.5 volts (V) halogen light found in certain otoscopes, and (b) if the magnification of a proposed extraction device met or exceeded the magnification of otoscopes used generally by skilled persons. Table 1 shows the list of top-level user needs, sub-user needs, and design inputs identified in the design traceability matrix.

TABLE 1

Design Traceability Matrix

| Top Level User Need # | Top Level User Needs | Sub User Need # | Sub User Needs | Source | Design Input # | Design Inputs |
|---|---|---|---|---|---|---|
| 1 | "able to visualize the working space" | 1.1 | "adequate amount of illumination" | physicians | 1.1.1 | "light source meets or exceeds 3.5 V halogen light found in an otoscope" |
|  |  | 1.2 | "adequate amount of magnification" | physicians | 1.2.1 | "magnification meets or exceeds the magnification of a standard otoscope" |
| 2 | "able to retrieve most common foreign bodies found in ears" | 2.1 | "device length long enough for auditory canal anatomy" | physicians/ engineers | 2.1.1 | "length to be inserted in auditory canal: 2.63 centimeters maximum" |
|  |  | 2.2 | "device ensures adequate fixation with a variety of foreign bodies" | physicians | 2.2.1 | "able to grab foreign bodies from a range of diameters" |
|  |  | 2.3 | "device is operable with a single hand" | physicians | 2.3.1 | "device is operable with a single hand" |
|  |  | 2.4 | "able to move freely in and out of pediatric auditory canal without harming auditory canal tissue" | physicians | 2.4.1 | "device contains smooth edges" |
| 3 | "biocompatible" | 3.1 | "no adverse effects to the auditory canal tissue during use" | physicians | 3.1.1 | "complies with ISO-10933" |
| 4 | "can't puncture or press hard against tympanic membrane" | 4.1 | "no exposed sharp edges involved in retrieval" | physicians | 4.1.1 | "exposed end of device only contains curved surfaces" |
|  |  | 4.2 | "adequate fixation with foreign body achieved with minimal applied pressure" | physicians/ engineers | 4.2.1 | "having an adjustable object grip radius or comprise flexible material with adhesive inside that could adhere to any object" |
| 5 | "intuitive and/or user friendly" | 5.1 | "minimum training required to operate" | physicians | 5.1.1 | "able to be used with provided instructions; is an attachment to preexisting medical equipment" |
|  |  | 5.2 | "simple user interface" | physicians/ engineers | 5.2.1 | "each actuator involves use of one finger only" |

The efficacy of three different proposed extraction device designs (not shown) were verified by comparing retrieval of different foreign bodies from an ear canal. The differing designs allowed for an adhesive material 40 to be applied to the proposed extraction device designs in various configurations (not shown). It was concluded that there was no significant difference between number of removal attempts between the three different proposed extraction device designs.

The extraction efficacy of nine further proposed extraction device designs (not shown) were evaluated using a black bean as a foreign body. Through use of nine different designs, three device parameters of interest were able to be modified: visualization, adhesion, and suction. The purpose of this testing was to determine which parameter best influenced the success rate of the tool. The statistical model created from these tests showed the adhesive parameter had significant impact on the device's removal success.

Example 2—Use of 3M 1567 Medical-Grade Synthetic Rubber Adhesive Material

Learning about the importance of selecting an adhesive material 40 was achieved through use of three different double-sided adhesive samples acquired from 3M Company (3M Center, St. Paul, Minnesota 55144, USA). The adhesives were applied to the extraction device embodiment to extract a single, pre-determined foreign body to be compared for relative efficiency of extraction. The 3M 1567 medical-grade synthetic rubber adhesive exhibited the highest tack, making it a preferred option for use as adhesive material 40 for removing a foreign body with a small dwell time.

After 3M 1567 was chosen as the adhesive to be used in a preferred embodiment of extraction device 10, four different adhesive profiles were tested with a single, pre-determined foreign body to be compared for relative efficiency. Two embodiments of adhesive material 40 each had a set of one or more adhesive apertures 94 having diameters of, respectively, about 1.00 mm (as shown in FIG. 5) and about 2.00 mm where it would cover extraction device 10 at apertured cap section 22 (as shown in FIGS. 7A, 7B, 7C, and 7D). For each adhesive aperture 94, adhesive material 40 would either be exposed on the sides of extraction device 10 or covered with Parafilm® tape to determine whether side adhesive was helpful or a hindrance.

It was found that the 1.00 mm adhesive aperture 94 was preferred, with surface 104 of tail portion 92 of adhesive material 40 being covered if tail surface 104 extended to intermediate section 20 and base section 24. The side of adhesive material 40 would adhere the sides of the ear canal model, making extraction both challenging and not so effective. The adherence and detachment of the adhesive with the canal walls would create erratic movement patterns, which would cause the foreign body to become detached from adhesive material 40 at cap section 22. Clinically, this would translate to pain and possible abrasion or tearing of a patient's external ear canal wall.

Verification testing of the 3M 1567 adhesive was performed using the 1.00 mm adhesive aperture 94 with surface 104 of tail portion 92 of adhesive material 40 being covered if tail surface 104 extended to intermediate section 20 and base section 24.

Figure 11A:
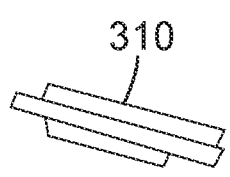
FIGS. 11A, 11B, and 11C are pictorial views of, respectively, a piece of balsa wood, a flat washer, and a plastic ball representing examples of foreign bodies that, with use of the disclosed extraction device, a clinician would extract from a patient's ear canal.
Figure 11B:
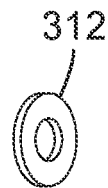
Figure 11:

FIGS. 11A, 11B, and 11C are pictorial views of, respectively, a piece of balsa wood, a flat washer, and a plastic ball placed into an ear canal model for extraction by an extraction device. As shown in FIGS. 11A, 11B, and 11C, verification testing comprised removing three varieties of foreign bodies: a piece of balsa wood 310, a flat washer 312, and a plastic ball 314 that were placed into the ear canal model (not shown) and were attempted to be extracted by a preferred embodiment of extraction device 10. As shown in FIG. 11A, the dimensions of balsa wood 310 were 7 mm×5 mm×3 mm. As shown in FIG. 11B, flat washer 312 was a SAE #2 washer. As shown in FIG. 11C, plastic ball 314 had a diameter of about 6.00 mm.

Average removal attempts for each object are summarized below in Table 2.

TABLE 2

| Average removal attempts for each object | Average Removal Attempts |
| --- | --- |
| Balsa Wood 310 | 1.87 |
| Washer 312 | 6.00 |
| Plastic Ball 314 | 1.53 |

REFERENCES

Adedeji, T. O., Sogebi O. A. & Bande S. (2016). Clinical spectrum of ear, nose and throat foreign bodies in North Western Nigeria. *Afr. Health Sci.* 16, 292-297.

FastStats—Emergency Department Visits. *Centers for Disease Control and Prevention*, Centers for Disease Control and Prevention, 19 Jan. 2017. How Much Does a Foreign Object from the Ear Removal (in office) Cost Near Me?

Heim, S. W., & Maughan, K. L. (2007). Foreign Bodies in the Ear, Nose, and Throat. *American Family Physician*, 76(8), 1185-1189.

Morris, S., Osborne, M., & McDermott, A. (2018). Will children ever learn? Removal of nasal and aural foreign bodies: a study of hospital episode statistics. *The Annals of The Royal College of Surgeons of England*, 100(8), 632-634.

Olson M. D., Saw J., Visscher S. L. & Balakrishnan K. (2018). Cost comparison and safety of emergency department conscious sedation for the removal of ear foreign bodies. *Int J Pediatr Otorhinolaryngol* 110, 140-143

Park J W, Jung J H, Kwak Y H & Jung J Y (2019). Epidemiology of pediatric visits to the emergency department due to foreign body injuries in South Korea. *Medicine (Baltimore)* 98, e15838.

It will be obvious to those having skill in the art that many changes may be made to the details of the above-described embodiments without departing from the underlying principles of the invention. The scope of the present invention should, therefore, be determined only by the following claims.

The invention claimed is:

1. A narrow-orifice foreign body extraction device configured as a unitary article, comprising:
a volumetric enclosure bounded by a frustoconical cone, the frustoconical cone having inner and outer surfaces and an intermediate section positioned between an apertured cap section and an apertured base section, the volumetric enclosure defining a central longitudinal axis that extends through the base, intermediate, and cap sections, the inner surface defining a boundary of an interior chamber of the volumetric enclosure, and the inner and outer surfaces defining between them a cone wall; and
an adhesive material secured to at least part of the inner or outer surfaces at the cap section, in which the cap section comprises a set of one or more cap apertures that extend through the cone wall.

2. The extraction device of claim 1, in which at least one section selected from the cap, intermediate, and base sections of the frustoconical cone is substantially shaped as a hyperboloid, pseudosphere, or parabolic cone.

3. The extraction device of claim 1, in which the interior chamber has a radius originating from the central longitudinal axis, the radius configured to increase continuously, incrementally, or both continuously and incrementally, along the length of the cone wall from the cap section to the base section to form a tapered cone.

4. The extraction device of claim 1, in which the cap section further comprises a perforated platform set within the interior chamber and in transverse relation to the central longitudinal axis.

5. The extraction device of claim 1, in which the cone wall at the cap section has a radius of curvature of about 2× R30.0 to about 2× R90.0.

6. The extraction device of claim 1, in which the cone wall at the intermediate or base sections has a radius of curvature of about 2× R10.0 to about 2× R70.0.

7. The extraction device of claim 1, in which the diameter of the interior chamber is about 1.00 mm to about 30.00 mm.

8. The extraction device of claim 1, in which the cone wall has a thickness of about 0.01 mm to 0.25 mm, about 0.25 mm to 0.75 mm, or about 0.75 mm or greater.

9. The extraction device of claim 1, in which the cone wall at the cap section forms an annular rim encompassing one or more of the cap apertures in the set of cap apertures, the annular rim having a radius of curvature of about 2× R0.10 to about 2× R1.00.

10. The extraction device of claim 1, in which each aperture in the set of cap apertures has a diameter of about 0.01 mm to 1.00 mm, about 1.00 mm to 2.00 mm, about 2.00 to 3.00 mm, about 3.00 mm to 4.00 mm, or about 4.00 mm or greater.

11. The extraction device of claim 1, in which the interior chamber of the frustoconical cone at the cap section has a diameter of about 1.00 mm to 2.00 mm, about 2.00 mm to 3.00 mm, about 3.00 mm to 4.00 mm, or about 4.00 mm or greater.

12. The extraction device of claim 1, in which the interior chamber of the frustoconical cone at the intermediate section has a diameter of about 1.00 mm to about 8.00 mm.

13. The extraction device of claim 1, in which the interior chamber of the frustoconical cone at the base section has a diameter of about 1.00 mm to about 30.00 mm.

14. The extraction device of claim 1, in which the base section comprises a set of one or more base apertures that extend through the cone wall.

15. The extraction device of claim 1, in which the base section is configured to form a friction fit with a head of an otoscope.

16. The extraction device of claim 1, in which the length of the frustoconical cone is about 25.00 mm to about 50.00 mm.

17. The extraction device of claim 1, in which the adhesive material comprises an apertured portion and a tail portion, the apertured portion having a set of one or more adhesive apertures and adhesive-covered opposing inner and outer side surfaces, and the tail portion having an adhesive-covered inner tail surface extending along and bonding to at least part of the outer surface at the cap section to secure the adhesive material to the cap section.

18. The extraction device of claim 17, in which at least one aperture in the set of adhesive apertures and at least one aperture in the set of cap apertures are substantially spatially aligned to provide an unobstructed sightline through the cap section and adhesive material.

19. The extraction device of claim 17, in which the apertured portion of the adhesive material has a length of about 1.00 mm to about 10.0 mm, a width of about 1.00 mm to about 10.0 mm, and a thickness of about 0.01 mm to about 2.00 mm.

20. The extraction device of claim 17, in which the tail portion of the adhesive material has a length of about 1.00 mm to about 50.0 mm, a width of about 0.01 mm to about 3.00 mm, and a thickness of about 0.01 mm to about 2.00 mm.

21. A vacuum adapter for providing negative pressure to a visualization device, comprising:
- a volumetric enclosure bounded by a tubular adapter body, the adapter body having an inner adapter surface defining a boundary of an interior chamber of the volumetric enclosure and an outer adapter surface, the inner and outer adapter surfaces defining between them an adapter wall; and
- a central longitudinal axis defined by the volumetric enclosure and extending through first and second adapter ends, the first adapter end configured to attach to the visualization device and the second adapter end configured to attach to a negative gas-pressure source to communicate relatively negative-pressurized gas through the extraction device of claim 1 and the visualization device to the negative gas-pressure source.

22. A system for extracting a foreign body from a narrow orifice comprising:
- an extraction device of claim 1;
- a visualization device configured to have an insufflation port and attach to the extraction device; and
- a vacuum adapter configured to attach to the insufflation port of the visualization device and communicate relatively negative-pressurized gas through the extraction device and the visualization device towards the negative gas-pressure source, thereby to facilitate removal of a foreign body from a narrow orifice.

23. The system of claim 22, in which the vacuum adapter is the vacuum adapter of claim 21.

\* \* \* \* \*